United States Patent [19]

Barnard, Jr. et al.

[11] 4,033,897

[45] July 5, 1977

[54] FLASH POINT DETERMINATION CALIBRATION STANDARDS

[75] Inventors: Alfred J. Barnard, Jr.; Russell C. Lance, Jr., both of Bethlehem, Pa.

[73] Assignee: J. T. Baker Chemical Company, Phillipsburg, N.J.

[22] Filed: Apr. 19, 1976

[21] Appl. No.: 678,228

[52] U.S. Cl. .......................... 252/408; 23/230 R; 23/230 HC; 23/230 M; 23/230 PC; 73/17 R; 73/36

[51] Int. Cl.$^2$ .............. C09K 3/00; G01N 25/52

[58] Field of Search ..... 23/230 R, 230 M, 230 HC, 23/230 PC; 252/408; 73/36, 17 R

[56] References Cited

UNITED STATES PATENTS

| | | | |
|---|---|---|---|
| 174,506 | 3/1876 | Everest | 23/230 HC |
| 2,303,265 | 11/1942 | Francis | 23/230 HC |
| 2,418,814 | 4/1947 | Ayers | 23/230 M |
| 2,527,121 | 10/1950 | Dudenbostel | 23/230 HC |
| 3,229,504 | 1/1966 | Smith | 73/36 |
| 3,293,905 | 12/1966 | Ratway et al. | 73/36 |
| 3,408,856 | 11/1968 | Gross | 73/17 R |

OTHER PUBLICATIONS

Phillips 66 Hydrocarbons, Phillips Petrol. Co., 6th Ed., Bulletin 522, pp. 31–33, 49–51, 56–58, 62–63, 66–68, 188, 192, 71–76, 78–79, 83, 91, 97–108, 111, 116–117, 125–126, (1964).

Meiter, E. G., "A Study of the Relation between Flash-Point and Vapor Pressure of Burning Oil", Abst. of Dissertation, pp. 3–21, OSU (1923), ATSM: D56-56, pp. 1–7, (1956).

The Merck Index, 8th Ed., pp. 137–138, 1122, 883, 431, 323, 298, (1968).

"Flammable Liquids, Gases and Solids", Associated Fact. Mutual Fire Insurance Companies, Loss Prevention Bull., No. 36.10, pp. 2–12, (1950).

Primary Examiner—Richard E. Schafer
Assistant Examiner—T. S. Gron
Attorney, Agent, or Firm—George W. Rauchfuss, Jr.; Eugene O. Retter

[57] ABSTRACT

Mixtures of compounds formulated as calibration standards for flash point determination at specific desired temperatures are provided. Components of similar structure, functionality, molecular weight and volatility, but exhibiting different flash points bracketing the temperature of the desired standard, are combined in predetermined appropriate ratios to provide a liquid calibration standard that does not exhibit any substantial change in flash point value on partial evaporation.

5 Claims, No Drawings

FLASH POINT DETERMINATION CALIBRATION STANDARDS

FIELD OF THE INVENTION

This invention relates to mixtures adapted as standards for flash point determinations.

DESCRIPTION OF THE PRIOR ART

The determination of the flash point of a flammable substance, and the associated methodology, has become a point of concern to those in many industries as a result of the adoption of regulations by the United States Department of Transportation — Hazardous Materials Regulations Board (39 FR 2768 and 40 FR 22263) and similar type regulations adopted by the United States Department of Labor — Occupational Safety and Health Administration. By said regulations of the Department of Transportations a flammable liquid is defined as a liquid exhibiting a flash point less than 100° F., a combustible liquid is defined as a liquid exhibiting a flash point of from 100° F. to 200° F. The Occupational Safety and Health Administration regulations classify flammable liquids into three categories: Class 1A — flash point less than 73° F., boiling point less than 100° F.; Class 1B — flash point less than 73° F., boiling point greater than 100° F.; and Class 1C — flash point equal to or greater than 73° F., boiling point unspecified.

The Department of Transportation regulations also specify approved flash point test methods such as Standard Method of Test for Flash Point by Tag Closed Tester (ASTM D 56-70) and Standard Method of Test for Flash Point of Liquids by Setaflash Closed Tester (ASTM D 3278-73). The ASTM currently calls for calibration of these flash point testers at 80° ± 1° F., using p-xylene of defined purity. However, it is known that the ASTM-specified p-xylene does not always give reproducible results, even when run on the same instrument by the same operator.

The relatively new regulations will effect entire industries especially the chemical industry and probably the most important criterion is the temperature interface between flammable and combustible liquids and, therefore, it is especially important to calibrate or ascertain the performance of a flash point tester at 100° F. Thus, it would be advantageous to have reliable calibrating standards exhibiting flash points at 80° F., 100° F. and 120° F. thereby allowing an operator to verify that his instrument is performing properly in the critical range. Additionally, since 73° F. and 200° F. are classification points reliable calibration standards at these temperatures are also desirable and needed. Also, since the regulations and the definitions therein may change from time to time it is desirable to be able to obtain reliable calibration standards at various temperatures in addition to the five set forth hereinbefore.

BRIEF SUMMARY OF THE INVENTION

A liquid calibration standard exhibiting a flash point at a definite, reproducible temperature is prepared by mixing in appropriate ratio substances exhibiting similar functionality and structure, molecular weight and volatility, but exhibiting different flash points bracketing the temperature of the desired standard. Such a calibration mixture is readily reproducible and would not be expected to exhibit any substantial change in the flash point value on partial evaporation.

DETAILED DESCRIPTION OF THE INVENTION

A flash point calibration liquid of this invention having a flash point at a desired temperature is prepared according to the following procedure. Having determined the desired temperature of the flash point calibration liquid wanted, one selects two organic liquids of similar functionality, structure, molecular weight, and volatility and exhibiting flash points bracketing the value desired, that is, one exhibiting a flash point temperature higher than the desired value and the other exhibiting a flash point temperature lower than the desired value. One then determines, according to an established flash point determination method such as the Setaflash Closed Tester Method (ASTM D 3278-73), the exact flash point for each component individually, and for several mixtures of said components, such as, for example, mixtures of the two components corresponding to 25%, 50% and 75%, on a weight basis, of the higher boiling component. After determining the flash point of these components and mixtures, one plots the flash point values versus concentration on Cartesian coordinates and draws a smooth curve through the plotted points. The approximate composition that will yield the calibration liquid of the desired flash point can then be read from the graph. For greater accuracy in obtaining a calibration liquid of a desired temperature one can read the approximate mixture from the graph and prepare that mixture and additionally two or more mixtures of said components differing slightly, for example, by up to about 10% by weight, from the mixture read off the graph. The other two or more mixtures will be course bracket the ratio of the mixture read off the graph. Then, after determining the flash point of these three mixtures, and plotting their values as before, a calibrated liquid exhibiting the exact flash point desired can be secured.

In a similar manner this procedure can be employed to obtain flash point calibration liquids of various desired temperatures within the range of the two liquids used. Additionally, this method can be extended by one skilled in the art to obtain flash point calibration liquid mixtures containing more than two component liquids.

It will be readily appreciated, of course, that the degree of similarity in molecular weight and volatility of the components of the liquid mixture standard is greater than a liquid mixture standard having a relatively low flash point than for a liquid mixture standard having a relatively high flash point. For example, the molecular weight and volatility of the components may vary by up to about 10% from each other for a liquid mixture standard having a flash point in the range of from about 73° to about 100° F. whereas the molecular weight and volatility of the components may vary by up to about 28% from each other for a liquid mixture standard having a flash point of from about 150° to about 200° F.

By employing the method set forth hereinbefore one can obtain definite, reproducible liquid calibration standards for desired temperatures. For example, utilizing such methods the following exemplary liquid calibration standard mixtures were prepared for the designated flash point standards desired.

EXAMPLE 1

73° F. Flash Point Calibration Standard

The components of similar functionality, structure, molecular weight and volatility selected to prepare a 73° F. standard were ethylbenzene, $C_8H_{10}$, molecular weight 106.17, boiling point 136° C., flash point 71° F., and vapor pressure 10 mm/26° C. and m-xylene, $C_8H_{10}$, molecular weight 106.17, boiling point 139° C., flash point 80° F., and vapor pressure 10 mm/28° C. The liquid calibration standard for 73° F. determined according to the hereinbefore described methodology is as follows:

| Component | Weight % |
|---|---|
| ethylbenzene | 76 |
| m-xylene | 24 |

EXAMPLE 2

100° F. Flash Point Calibration Standard

A liquid calibration standard for 100° F. was similarly prepared from p-xylene, $C_8H_{10}$, molecular weight 106.17, boiling point 138° C., flash point 78° F., vapor pressure 10 mm/27° C. and oxylene, $C_8H_{10}$, molecular weight 106.17, boiling point 144° C., flash point 115° F., vapor pressure 10 mm/32° C. and had the following composition:

| Component | Weight % |
|---|---|
| p-xylene | 44 |
| o-xylene | 56 |

EXAMPLE 3

100° F. Flash Point Calibration Standard

A liquid calibration standard for 100° F. was similarly prepared from isopropylbenzene (cumene), $C_8H_{12}$, molecular weight 120.20, boiling point 52° C., flash point 88° F., vapor pressure 10 mm/38° C. and 1,2,4-trimethylbenzene (psuedo-cumene), $C_9H_{12}$, molecular weight 120.20, boiling point 169° C., flash point 117° F., vapor pressure 10 mm/35° C. and had the following composition:

| Component | Weight % |
|---|---|
| cumene | 50 |
| psuedo-cumene | 50 |

EXAMPLE 4

120° F. Flash Point Calibration Standard

A liquid calibration standard for 120°F. was similarly prepared from 1,2,4-trimethylbenzene (psuedo-cumene), $C_9H_{12}$, molecular weight 120.20, boiling point 169° C., flash point 117° F., vapor pressure 10mm/35° C. and decahydronaphthalene (decalin), $C_{10}H_{18}$, molecular weight 138.25, boiling point 187° C., flash point 128° F., vapor pressure 10mm/47° C. and had the following composition:

| Component | Weight % |
|---|---|
| psuedo-cumene | 50 |
| decalin | 50 |

EXAMPLE 5

200° F. Flash Point Calibration Standard

A liquid calibration standard for 200° F. was similarly prepared from benzyl alcohol, $C_7H_8O$, molecular weight 108.14, boiling point 205° C., flash point 193° F., vapor pressure 1 mm/58° C. and 3-phenyl-1-propanol, $C_9H_{12}O$, molecular weight 136.20, boiling point 219° C., flash point 207° F., vapor pressure 10 mm/100° C. and had the following composition:

| Component | Weight % |
|---|---|
| benzyl alcohol | 80 |
| 3-phenyl-1-propanol | 20 |

Such calibration liquid standards may, if desired, have one or more appropriate dyes added thereto for color-coding of the different temperature standards so as to prevent erroneous use of the wrong standard. The dye content necessary to produce the desired color is small and does not affect the flash point of the liquid standard.

We claim:

1. A flash point determination reference standard calibration mixture for a flash point calibration temperature of 73° F., said standard calibration mixture not exhibiting any substantial change in the flash point value on partial evaporation of the mixture and consisting essentially of a mixture of about 76% by weight ethylbenzene and about 24% by weight m-xylene.

2. A flash point determination reference standard calibration mixture for a flash point calibration temperature of 100° F., said standard calibration mixture not exhibiting any substantial change in the flash point value on partial evaporation of the mixture and consisting essentially of a mixture of about 44% by weight p-xylene and about 56% by weight o-xylene.

3. A flash point determination reference standard calibration mixture for a flash point calibration temperature of 100° F., said standard calibration mixture not exhibiting any substantial change in the flash point value on partial evaporation of the mixture and consisting essentially of a mixture of about 50% by weight 1,2,4-trimethylbenzene and about 50% by weight isopropylbenzene.

4. A flash point determination reference standard calibration mixture for a flash point calibration temperature of 120° F., said standard calibration mixture not exhibiting any substantial change in the flash point value on partial evaporation of the mixture and consisting essentially of a mixture of about 50% by weight 1,2,4-trimethylbenzene and about 50% by weight decahydronaphthalene.

5. A flash point determination reference standard calibration mixture for a flash point calibration temperature of 200° F., said standard calibration mixture not exhibiting any substantial change in the flash point value on partial evaporation of the mixture and consisting essentially of a mixture of about 80% by weight benzyl alcohol and about 20% by weight 3-phenyl-1-propanol.

* * * * *